US011123572B2

(12) United States Patent
Dijkstra et al.

(10) Patent No.: US 11,123,572 B2
(45) Date of Patent: Sep. 21, 2021

(54) EYEWEAR PHOTOTHERAPY DEVICE FOR EYE COSMETOLOGY

(71) Applicant: ShenZhen Kaiyan Medical Equipment Co, LTD, Shenzhen (CN)

(72) Inventors: Alain Dijkstra, Amstelveen (NL); Jonathan James Knight, Kent (GB); Jooeun Kim, Seoul (KR); Yong Zhang, Changde (CN); Dan Xu, Shenzhen (CN)

( * ) Notice: Subject to any disclaimer, the term of this patent is extended or adjusted under 35 U.S.C. 154(b) by 58 days.

(21) Appl. No.: 15/972,082

(22) Filed: May 4, 2018

(65) Prior Publication Data

US 2019/0126060 A1  May 2, 2019

(51) Int. Cl.

| F21L 4/02 | (2006.01) |
| A61N 5/06 | (2006.01) |
| F21V 33/00 | (2006.01) |
| F21V 23/00 | (2015.01) |
| F21V 23/04 | (2006.01) |
| F21L 4/08 | (2006.01) |
| G02C 11/04 | (2006.01) |
| G02C 11/00 | (2006.01) |

(Continued)

(52) U.S. Cl.
CPC .............. *A61N 5/0616* (2013.01); *F21L 4/02* (2013.01); *F21L 4/08* (2013.01); *F21V 23/003* (2013.01); *F21V 23/04* (2013.01); *F21V 33/0004* (2013.01); *G02C 11/04* (2013.01); *A61N 2005/0626* (2013.01); *A61N 2005/0648* (2013.01); *A61N 2005/0652* (2013.01); *A61N 2005/0659* (2013.01); *A61N 2005/0663* (2013.01); *F21W 2131/20* (2013.01); *F21Y 2115/10* (2016.08); *G02C 11/10* (2013.01)

(58) Field of Classification Search
CPC .... A61N 5/0613; A61N 5/062; A61N 5/0618; G02C 5/00; G02C 11/06; G02C 11/04; G02C 11/02; G02C 1/04; A61C 19/004; A61M 21/02; A61Q 19/02
USPC ......... 606/4; 604/20; 351/113, 158, 51, 124; 607/90, 93, 88; 433/215
See application file for complete search history.

(56) References Cited

U.S. PATENT DOCUMENTS

| 5,835,185 A * | 11/1998 | Kallman .................. G02C 5/00 351/113 |
| 6,145,983 A | 11/2000 | Schiffer |
| 6,908,195 B2 | 6/2005 | Fuller |

(Continued)

*Primary Examiner* — Ankit D Tejani
*Assistant Examiner* — Joshua Brendon Solomon
(74) *Attorney, Agent, or Firm* — Emanus, LLC; Willie Jacques (57) ABSTRACT

The present disclosure relates to an eyewear phototherapy device for providing skin cosmetology to the skin surrounding the eyes. The device includes a main spectacle frame having a left supporting member and right supporting member, each including at least one housing assembly extending outward from the each supporting member and facing towards the inner portion of the supporting member. Each of the housing assemblies includes an LED light board, attached to the inner side of the respective housing assembly, which is adapted to emit light energy, a transparent silicone cover attached on the LED light board for protecting direct contact between the LED light board and human skin, a protective element which is adapted to spread the LED emissions around a human eye and provide protection to the human eye from the LED emissions.

19 Claims, 5 Drawing Sheets

(51) Int. Cl.
*F21W 131/20* (2006.01)
*F21Y 115/10* (2016.01)

(56) References Cited

U.S. PATENT DOCUMENTS

| | | | |
|---|---|---|---|
| 7,147,319 B2 | 12/2006 | Lin | |
| 2001/0052962 A1* | 12/2001 | Yang | G02C 1/04 |
| | | | 351/124 |
| 2005/0278003 A1* | 12/2005 | Feldman | A61N 5/0618 |
| | | | 607/88 |
| 2006/0235346 A1* | 10/2006 | Prescott | A61N 5/0616 |
| | | | 602/2 |
| 2007/0013865 A1* | 1/2007 | Jordan | G02C 11/04 |
| | | | 351/158 |
| 2010/0228689 A1 | 9/2010 | Hall | |
| 2012/0162598 A1 | 6/2012 | Tsubota et al. | |
| 2012/0203310 A1 | 8/2012 | Pugh et al. | |
| 2012/0215291 A1* | 8/2012 | Pugh | A61M 21/02 |
| | | | 607/93 |
| 2013/0066404 A1 | 3/2013 | Tapper et al. | |
| 2013/0215374 A1* | 8/2013 | Blum | G02C 11/06 |
| | | | 351/158 |
| 2015/0018751 A1* | 1/2015 | Kerber | A61N 5/062 |
| | | | 604/20 |
| 2015/0230988 A1 | 8/2015 | Chao et al. | |
| 2016/0004103 A1* | 1/2016 | Reyes | G02C 11/02 |
| | | | 351/51 |
| 2016/0016004 A1* | 1/2016 | Hudson | A61N 5/0618 |
| | | | 607/90 |
| 2016/0067026 A1* | 3/2016 | Esfandiari | A61C 19/004 |
| | | | 433/215 |
| 2016/0067087 A1* | 3/2016 | Tedford | A61N 5/0613 |
| | | | 606/4 |
| 2016/0310324 A1 | 10/2016 | Jung et al. | |

* cited by examiner

EYEWEAR PHOTOTHERAPY DEVICE FOR EYE COSMETOLOGY

FIELD OF DISCLOSURE

The present disclosure relates to the field of providing skin cosmetology for removing wrinkles on the skin. More specifically, the disclosure relates to an eyewear phototherapy device for providing eye cosmetology, anti-aging treatment, anti-wrinkle treatment and other skin related treatments around the eye.

BACKGROUND

In general, phototherapy for the treatment of skin diseases advantageously uses light to promote biochemical reactions in the skin. Phototherapy is an optical medical technology for the treatment of damaged skin and uses a variety of light sources, such as daylight, laser, and fluorescent light for the regeneration or destruction of skin tissue. In recent years, phototherapy is used to treat skin diseases; however, it is widely used in skin beautification treatments as well.

In U.S. Pat. No. 5,503,637 Kyricos et al. disclose a portable apparatus for producing and delivering high-intensity white light to the eyes in order to modify the subject's circadian phase. The apparatus is shown in the form of a sports visor having a high intensity cold cathode fluorescent lamp imbedded in the underside. The light is filtered so that unwanted frequencies of light are not radiated to the subject's face. A controller is provided which is programmed to deliver an amount of light determined to treat a circadian rhythm disorder. The apparatus, however, is fragile, bulky, expensive, and cannot be used while asleep, with eyes open, or without attracting attention.

In U.S. App. Pat. No. US20050278003A1 Harold Feldman disclose Wearable devices including a hat or cap, eyeglasses, an eye mask, or a face mask deliver light from light-emitting diodes or deliver electroluminescent light from a light source including an electroluminescent wire or flat panel powered by an inverter connected to the hat or cap, the eyeglasses, the eye mask, or the face mask. The delivery of the light is for entertainment or therapeutic purposes. Delivery of therapeutic light to the retinal area or to the skin of the user by a wearable device, without the use of the hands of the user, applies consistent levels of the therapeutic light to relax the user, to remove wrinkles in the skin, and to impart other healing effects. A sufficient amount of lux at appropriate optical wavelengths is generated to be incident for long periods upon the retina of the user or upon the skin of the user for healing effect. The light source is fixed to a head-mounted apparatus. The apparatus, however, is fragile, bulky, interferes with normal vision, and cannot be used without attracting attention.

Lastly, particularly in therapeutic devices treating facial areas, eye protection is needed to avoid light damage or irritation to a patient's eyes, which are not useful for broad coverage of lesion areas.

Dual-LED light treatment, however, provides "proper' light output which illuminates large lesion areas in comparison. LED is also advantageous in that it provides treatment similar to converting sunlight for plant cell stimulation. As with the sun, dual-LED behaves in a way to induce photo-biochemical reactions between skin cells offering superior therapeutic treatment. The skin treatment technique using LED light sources is similar to the principle of converting the sun into plant cells by the chlorophyll in plants. Such LED lights also induce photo-biochemical reactions between skin cells.

Light therapy using LED light capitalizes on the fact that photons of LED light sources are absorbed into the pigment or photoreceptors in the cell tissue, and absorbed by the cells increases the synthesis of reactive oxygen species (ROS) and adenosine triphosphate (ATP) in the cell tissue, and nitrogen oxide (NO) is released by cells exposed to red and near-infrared light. At selected wavelengths and wavelengths of light, light is absorbed by photoreceptors, such as cytochrome C oxidase, photolytically inhibiting NO, promoting enzyme activation, promoting mitochondrial metabolism and ATP production. As a result, proteins such as hemoglobin and myoglobin release extra NO, which is caused by a continuous intracellular biochemical reaction. Therefore, LED light irradiates cells with the overall metabolic activity of activated cells and plays a major role in cell regeneration and rehabilitation. In addition, LED lighting can promote the production of collagen and elastin in the skin, inhibit the generation of wrinkles, thereby making the skin moist and elastic.

There is further need to reduce the inconvenience for the users by using a silicone resin covering portion and preventing the eyes not to come in direct contact with the light portion. The existing LED light glasses/spectacular devices are considered to be harmful to eyesight.

LED Phototherapy reduces fine lines and wrinkles in the eyes, but there are much more benefits. It helps to reduce age spots and skin discoloration. Other skin problems can be treated with different techniques of phototherapy. More and more people are turning to use the natural method to solve their skin problems and utilize the way of safe and painless treatments.

However, the phototherapy devices currently used in treat dermatological and cosmetic skin care are bulky and expensive. So the treatment of dermatological or cosmetic dermatology with phototherapy requires a well-equipped hospital or beauty salon with lights. In addition, masks and other devices capable of providing light cannot be applied to a particular area which needs to be treated. These apparatuses are bulky, difficult to use, not portable, and cannot be used on open eyes.

Accordingly, there is a need to solve the above problems, and provide an LED light therapy that can provide a dedicated eyewear LED light spot that can be conveniently used and readily adaptable to communicate therapeutic light to areas near the eyes, particularly with regard to anti-aging treatments, and protect the patient's eyes.

SUMMARY OF THE DISCLOSURE

It should be understood that this disclosure is not limited to the particular device, and methodologies described herein, as there can be multiple possible embodiments of the present disclosure which are not expressly illustrated in the present disclosure. It is also to be understood that the terminology used in the description is for the purpose of describing the particular versions or embodiments only and is not intended to limit the scope of the present disclosure.

In an aspect, the present disclosure provides an eyewear phototherapy device for providing skin cosmetology. The device comprises a main spectacle frame having a left supporting member and a right supporting member, such that the left supporting member and the right supporting member include at least one housing assembly extending outward from the each supporting member and facing the left and the right supporting members, respectively. Each of the housing assembly comprises an LED light board which is adapted to emit LED light and attached to the inner side of the housing assembly; a transparent silicone cover attached on the LED light board for protecting direct contact between the LED light board and human skin; a controller circuit board connected to the LED light board; at least one control button; a battery unit and at least one protective element which is configured at one end of each housing assembly.

In an aspect, the controller circuit board is capable of controlling emissions from the LED light board. Further, the controller circuit board includes a one control button for receiving a user input, wherein the control button is connected to the control board. Further, the battery unit located within the housing assembly is adapted to provide power to the LED light board, the controller circuit board and the at least one control button. Further, the protective elements which are configured at one end of each housing assembly, are adapted to spread the LED emissions around a human eye and provide protection to the human eye from the LED emissions.

In an aspect of the present disclosure, the controller circuit board is adapted to receive the user input from the at least one first control button and activate the LED light board to deliver emissions based on the user input.

In yet another aspect of the present disclosure, the left supporting member and the right supporting member include a curved left nose arm and a curved right nose arm extending downward, respectively, such that the curved left nose arm and the curved right nose arm upon connecting create a nose support at the joining point. The left supporting member, the curved left nose arm, and a left lens support create a left receptacle. The right supporting member, the curved right nose arm, and a right lens support create a right receptacle. The left receptacle and the right receptacle are adapted to accommodate a user desired glass or lens. The left lens support and the right lens support are flexible/adjustable which helps in accommodating the user desired glass or lens within the left receptacle and the right receptacle, respectively.

The foregoing has broadly outlined the features and technical advantages of the present disclosure in order that the detailed description of the disclosure that follows may be better understood. Additional features and advantages of the disclosure will be described hereinafter which form the subject of the claims of the disclosure. It should be appreciated that the conception and specific embodiments disclosed may be readily utilized as a basis for modifying or designing other structures for carrying out the same purposes of the present disclosure. It should also be realized that such equivalent constructions do not depart from the disclosure as set forth in the appended claims. The novel features which are believed to be characteristic of the disclosure, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present disclosure.

BRIEF DESCRIPTION OF THE DRAWINGS

For a complete understanding of the present disclosure, the invention can be better understood with reference to the following figures.

DETAILED DESCRIPTION OF THE DISCLOSURE

Embodiments of the present disclosure will be described more fully hereinafter with reference to the accompanying drawings in which like numerals represent like elements throughout the several figures, and in which example embodiments are shown. Embodiments of the present invention may, however, be embodied in many different forms and should not be construed as limited to the embodiments set forth herein. The examples set forth herein are non-limiting examples and are merely examples of other possible examples. Like numerals refers to like elements throughout the present disclosure.

The present disclosure relates generally, as indicated, to an eyewear phototherapy device 200 for providing skin cosmetology to the skin surrounding the eyes. The device 200 includes a main spectacle frame 100 having a left supporting member 100L and a right supporting member 100R, such that the left supporting member 100L and the right supporting member 100R include at least one housing assembly (105L, 105R) extending outward from the each supporting member (i.e., left and right supporting members, respectively) and face towards the inner portion of the supporting member. Each of the housing assembly (105L, 105R) includes an LED light board (2, 2a) attached to the inner side of the housing assembly (105L, 105R) which is adapted to emit LED light; a transparent silicone cover (3, 8) attached on the LED light board (2, 2a) for protecting direct contact between the LED light board (2, 2a); and human skin, a first protective element 4 configured at one end of the left supporting member 105L, a second protective element 7 configured at one end of the right supporting member 105R, wherein both protective elements 4, 7 guide the led emission around the eyes and prevent the eye from the LED irradiation or emission; a first controller circuit board 9 connected to the LED light board (2, 2a); a battery unit 1; and a first control button 11. The first controller circuit board 9 is capable of controlling emissions from the LED light board (2, 2a) located in the each of the housing assembly (105L, 105R). The first control button 11 having a cover 11a configured in the housing assembly 105R for receiving a user input, wherein the first control button 11 is connected to the first controller circuit board 9. The first battery unit 1 is adapted to provide power to each LED light board (2, 2a), the first controller circuit board 9 and the control button. The each of the housing assembly (105L, 105R) includes at least one protective element which is adapted to spread the LED emissions around a human eye and provide protection to the human eye from the LED emissions.

In one embodiment, the LED light may emit red, white, blue and green lights which are particularly useful for anti-aging treatment. They promote the increased production of collagen, the protein responsible for firm and elastic skin. LED red light also increases blood vessels by creating new capillaries. Devices that utilize LED red light provide increased blood flows to tissues, where such blood flow carries nutrients that help to repair the skin.

Figure 1:
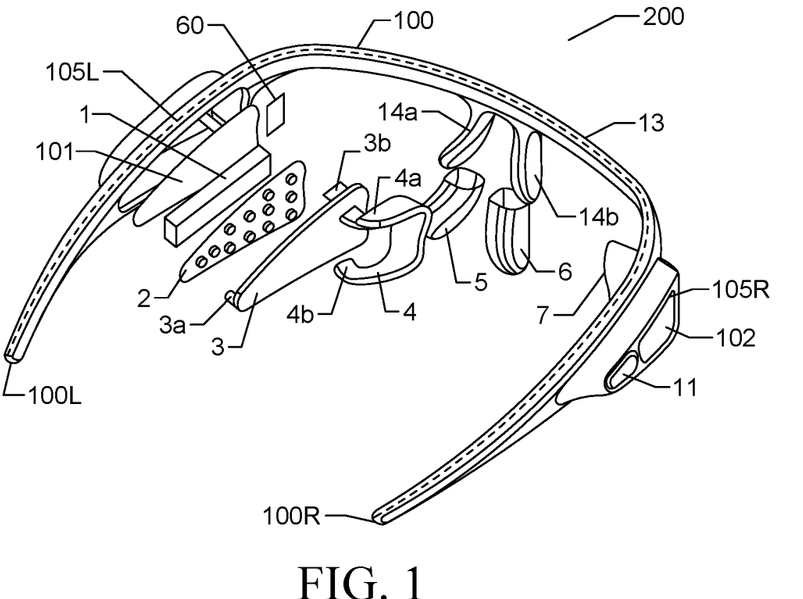
FIG. 1 delineates a perspective view of an eyewear phototherapy device with exploded view of a left housing assembly, according to various embodiments of the present disclosure.
Figure 2:
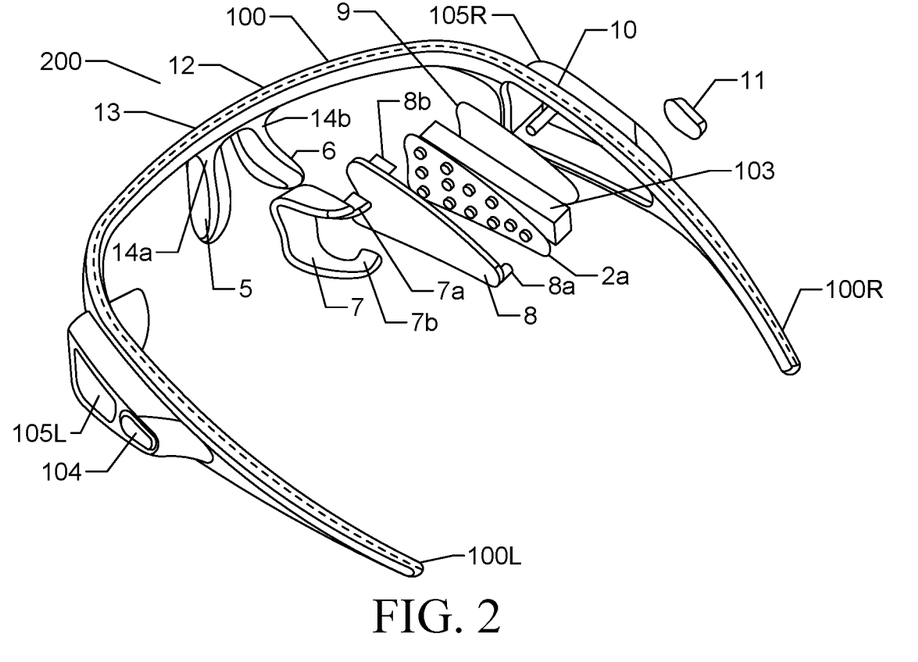
FIG. 2 delineates a perspective view of the eyewear phototherapy device with exploded view of a right housing assembly, according to various embodiments of the present disclosure.

Referring to FIGS. 1 and 2 of the accompanying drawings, there are shown two different exploded views of the eyewear phototherapy device. There is shown the main spectacle frame 100 of the eyewear phototherapy device 200. As shown, the main spectacle frame 100 resembles the shape of a spectacle having two supporting arms 100L and 100R. The main spectacle frame 100 is usually made up of plastic material and has flexible supporting arms 100L and 100R to get adjusted and fit on the eyes of different persons with varying sizes of the eye region. The main spectacle frame 100 can also be made from non-conductive materials and not limited to plastics.

In an embodiment, the two supporting arms 100L and 100R are connected with a middle joint portion 12 to create the main spectacle frame 100. The main spectacle frame 100 comprises a hollow tube 13 throughout its body. The hollow tube 13 stretches from the free end of the left supporting arm 100L to the free end of the right supporting arm 100R.

The hollow tube 13 includes electrical conducting wires throughout for connecting the various components of the eyewear phototherapy device 200. The conducting wires act as connecting wires for connecting the various components as discussed herein below.

The FIG. 1 and FIG. 2 illustrates an embodiment of the present disclosure where an exploded view of the left housing assembly 105L and an exploded view of the right housing assembly 105R are shown, respectively. There is shown the battery unit 1 which is provided in the left housing assembly 105L. The battery unit 1 is preferably a lithium battery, however, may be another power source. The battery unit 1 is connected to the LED light board 2 and the LED light board 2a, wherein the battery unit 1 is connected the LED light board 2a via connecting wires present in the hollow tube 13. The LED light board 2 and the LED light board 2a emits visible light of wavelengths of 680 nm and 630 nm and 605 nm, and a wavelength of 880 nm of near infrared light. The lithium batteries can be repeatedly charged and discharged so as to be reusable as per requirement of the user.

In one embodiment, the eyewear phototherapy device 200 includes at least one USB port (not shown) which is connected to the battery unit 1 for charging the battery unit 1 via external power source through a USB cable. The USB port is also connected to the controller circuit board (CCB) 9. The USB port is female USB-C port which is adapted to receive a male USB-C connector of the USB cable and establish an electronic connection between the female USB port and male USB connector, wherein changing cable is connected to the external charging source.

In an embodiment, the LED light board 2 and the LED light board 2a can be powered by an external power source (not shown). The LED light board 2 and the LED light board 2a is covered with a transparent silicon cover 3 and 8, respectively, so that the irradiation amount (visible light of wavelengths of 680 nm and 630 nm and 605 nm and a wavelength of 880 nm of near infrared light.) can be increased, while maintaining comfort for a user. In addition, the silicon covers 3 and 8 is added to protect the user's eyes from light output by preventing direct contact between the LED light board and human skin.

The eyewear phototherapy device 200 and the transparent silicon covers 3 and 8 use endothelial material which is a transparent PC (polycarbonate) material, and the light and wavelength of the LED can be transmitted through the material. In addition, the characteristic of the LED light board (2, 2a) is that the multiple LED elements operated by the supply of the first battery unit 1 are assigned to specific areas of the skin surrounding the eyes. The internal and external features of detachable eyeglasses are perforated on both sides. In addition, the eye openings and nose support are formed around the center of the eyeglasses and closely adhere to the contour of the face.

The LED light board 2, the LED light board 2a and the at least one user input button are connected with a controller circuit board (CCB) 9 as shown in FIG. 2, wherein the LED light board 2 and the battery unit 1 is connected to the controller circuit board (CCB) 9 via the connecting wire configured within the hollow tube 13. The first controller circuit board 9 controls the LED light board 2, the LED light board 2a and the battery unit 1. The first controller circuit board 9 is adapted to control the amount of light, LED light board (2, 2a) emits, the operating time of the eyewear phototherapy device 200 and more. The first controller circuit board 9 is further configured to control the amount of charge, the voltage of the battery unit 1.

The first controller circuit board 9 is configured to control range of LED light emissions or light energy of both the LED light board 2 and the LED light board 2a based on the user input separately.

The at least one housing assembly 105L of the left supporting member 100L includes the first battery unit 1, the first LED light board 2, the first transparent silicon cover 3 and the at least one first protective element 4.

As shown in FIG. 2, the at least one housing assembly 105R of the right supporting member 100R includes the first control button 11 connected with the first controller circuit board 9 and the second LED light board 2a, the second transparent silicon cover 8 and the at least one second protective element 7.

The first control button 11, the first controller circuit board 9, the first battery unit 1, the first LED light board 2, the second LED light board 2a are interconnected via connecting wire such that the first controller circuit board 9 is adapted to control the first battery unit 1, the first LED light board 2, the second LED light board 2a based on the user input received from the first control button 11. The first control button 11 placed below a button cover 11a, wherein the button cover 11a is configured within the housing assembly 105R.

In an embodiment, the first control button 11 is adapted to receive input from the user.

In an embodiment, a second controller circuit board 101 further includes a communication unit 60 which is adapted to communicate with other computing devices via communication means such as Bluetooth, NFC etc. In such scenario, the user may operate the eyewear phototherapy device 200 using his mobile phone. It will be apparent to persons skilled in the art that the mobile phone could relate to any portable computing device such as a tablet, a smart phone and the like. The first controller circuit board 9 include a microcontroller or processors, registers, memory, sensors and the combination thereof. The first controller circuit board 9 may include embedded software application for executing various functions.

The first controller circuit board 9 connected to a display 102 attached to the outer surface of the housing assembly 105R for displaying at least one information to the user. The display 102 is connected to the first controller circuit board 9 and the first control button 11.

The information display 102 displays a user selection mode such as low, medium and high, time duration of the therapy, type of alarm icon and the combination thereof.

In an embodiment, the user can select the intensity of the LED emissions from at least one of low, medium or high mode.

In an embodiment, the eyewear phototherapy device 200 includes an audio device for providing audio alert notification based on predefined parameter. The audio device is connected to the first controller circuit board 9.

The predefined parameter belongs to any one of low battery, expiration of therapy time, communication establishment notification, and failure of apparatus component, battery replacement and combinations thereof.

The first control button 11 allow users to set time duration of the therapy. It may happen that a user requires therapy say only for 30 seconds. The user may set the time duration and once the duration is complete, the eyewear phototherapy device 200 stops automatically.

In an embodiment, the left supporting member 100L and the right supporting member 100R includes a curved left nose arm 14a and a curved right nose arm 14b extending downward respectively (shown in FIG. 4A) to a joining point or a connecting point 12. The curved left nose arm 14a and the curved right nose arm 14b upon connecting at the connecting point 12 create a nose support below the connecting point 12. The curved left and right nose arms (14a, 14b) are essentially made up of silicone material to provide comfortable wearing to the user. The curved left and right nose arms (14a, 14b) are characterized by the use of silica gel materials helps in protecting the eyes and eyesight.

As can be seen from FIG. 1, in the left portion of the spectacle frame 100 which is supposed to be placed on the left eye and which has the left supporting member 100L, the curved left nose arm 14a, and the left lens support 5 create the left receptacle for holding or accommodating a user desired glass or lens.

Similarly, as shown in FIG. 2 in the right portion of the spectacle frame 100 supposed to be placed on the right eye and which has the right supporting member 100R, the curved right nose arm 14b, and the right lens support 6 create a right receptacle for holding or accommodating a user desired glass or lens.

The left lens support 5 and the right lens support 6 are flexible and adjustable which helps in accommodating the user desired glass or lens within the left receptacle and the right receptacle, respectively.

In an embodiment, the first protective element 4 which is provided in the left portion of the spectacle frame 100 includes fixing elements 4a and 4b (shown in FIG. 1) for fixing the first protective element 4 with the left housing assembly 105L.

Similarly, the second protective element 7 which is provided in the right portion of the spectacle frame 100 includes fixing elements 7a and 7b (shown in FIG. 2) for fixing the second protective element 7 with the right housing assembly 105R.

In an exemplary embodiment, the housing assembly 105L on left supporting arm 100L and the housing assembly 105R on the right supporting arm 100R are adapted to function independent of each other.

In exemplary embodiment, the housing assembly 105L on the left supporting arm 100L may include the first battery unit 1; [the first LED light board 2; the first transparent silicon cover 3 attached to the first LED light board 2; the first protective element 4; and, the second controller circuit board 101 and a second control button 104 operable by a user.

A user may operate the housing assembly 105L on the left supporting arm 100L with the help of the second control button 104 and the second control button 104 will function the same way as the first control button 11 described above with reference to FIG. 2.

Additionally, the second controller circuit board 101 further includes a communication unit 60 which is adapted to communicate with other computing devices via communication means such as Bluetooth, NFC etc. In such scenarios, the user may operate the eyewear phototherapy device 200 only on the left eye using his mobile phone. It will be apparent to persons skilled in the art that the mobile phone could relate to any portable computing device such as, a tablet, a smart phone and the like.

The first control button 11 allows users to set time duration of the therapy. It may happen that a user requires therapy say only for 30 seconds. The user may set the time duration and once the duration is complete, the eyewear phototherapy device 200 stops automatically for the left portion of the eyewear phototherapy device 200.

There is provided a left curved nose arm and a left lens support for creating a receptacle for holding a left lens over the left eye of the user.

In such scenario, the first LED light board emits light energy as per input from the user only with respect to the left eye whereas the same shall not apply to the assembly on the right supporting arm.

In another variation of the exemplary embodiment, the housing assembly 105R in the right supporting arm 100R comprises of second battery unit 103; the second LED light board 2a; the second transparent silicon cover 8 attached to the second LED light board 2a; the second protective element 7; and the first controller circuit board 9 and the first control button 11 operable by a user.

A user may operate the housing assembly 105L on the left supporting arm 100L with the help of the second control button 104 at left housing assembly 105L. The operation of the housing assembly 105L with the help of the second control button 104 will function the same way as operation of the first control button 11 at the right housing assembly 105R described above with reference to FIG. 2.

There are situations when the LED emission requirements for the skin surrounding the left eye and the skin surrounding the right eye are different. Therefore, the present embodiment enables the user to control and use both the sides of the eyewear phototherapy device 200 in an independent manner.

The eyewear phototherapy device 200 is designed for users to use eyewear phototherapy device 200 in same fashion as spectacle, goggles or eyeglasses. The eyewear phototherapy device 200 provides a treatment of eye tail area or area around the eye for eye care and treatment, and nasal bridge silicone provided in the body of eyewear phototherapy device 200 can make people much more comfortable to use the eyewear phototherapy device 200. The light silica gel light barrier (4, 7) covers the light source as it spread the light around the eye area and prevents the LED emissions to fall in the eyes, thereby effectively protecting the eyes.

As described above, according to the present invention, it is possible to provide an LED light treatment wearable eyewear device that can be used as if wearing glasses regardless of the shape and size of the user's face and can be conveniently used regardless of the place.

The above described eyewear phototherapy device 200 can be conveniently disassembled and install the silicone sleeve according to the user's needs.

In particular, the present invention can help to manage much effectively for the wrinkles of the user's eyes by LED lights that emit near-infrared light and visible red light.

Figure 3:
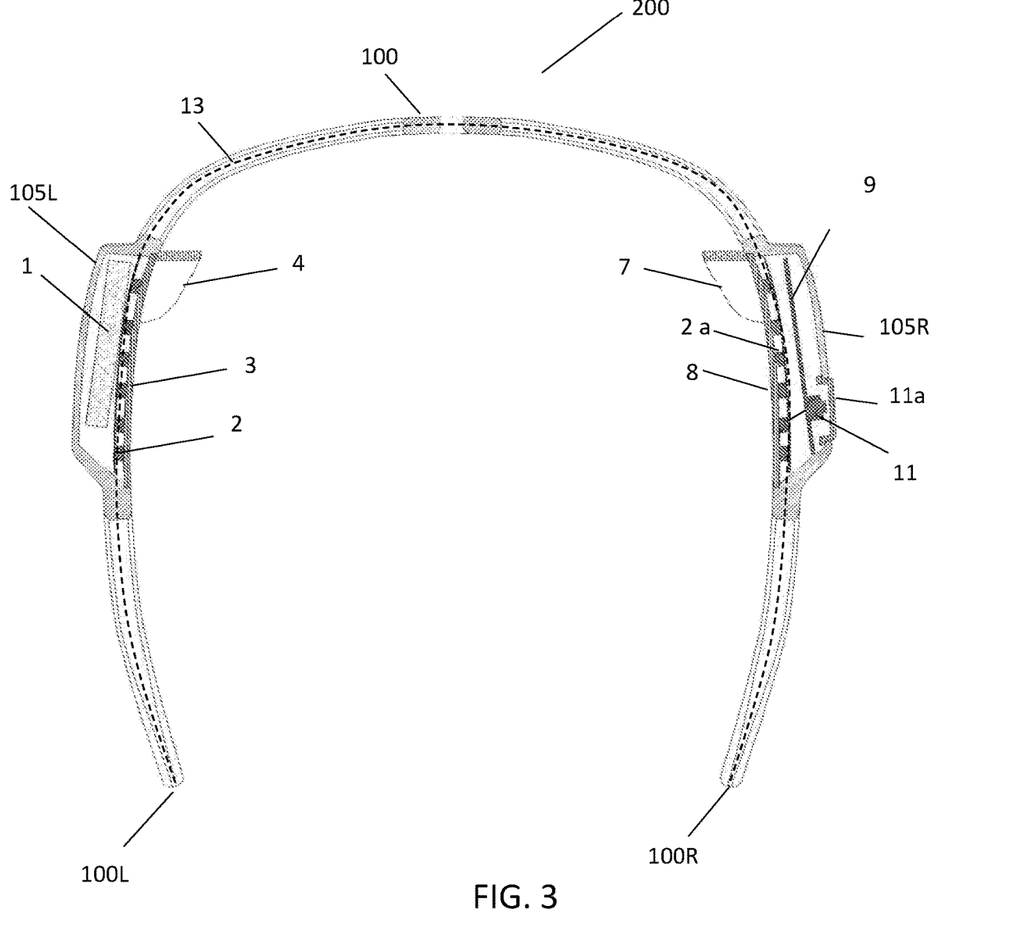
FIG. 3 delineates a top view of the eyewear phototherapy device, according to various embodiments of the present disclosure FIGS. 4a-4b delineate various cross-sectional views of the eyewear phototherapy device, according to various embodiments of the present disclosure.

Referring to FIG. 3, there is shown a top view of the eyewear phototherapy device 200. The top view clearly illustrates the various components such as the LED light board 2 and the LED light board 2a in the left and right housing assemblies (105R, 105L), the first control button 11 at right housing assembly 105R, the battery unit 1 at left housing assembly 105L, the light silica gel light barriers (4, 7) covers and the transparent protective silicon covers 3 and 8 at the left and the right housing assembly (105L, 105R) and the two supporting arms 100L and 100R respectively.

Figure 4A:
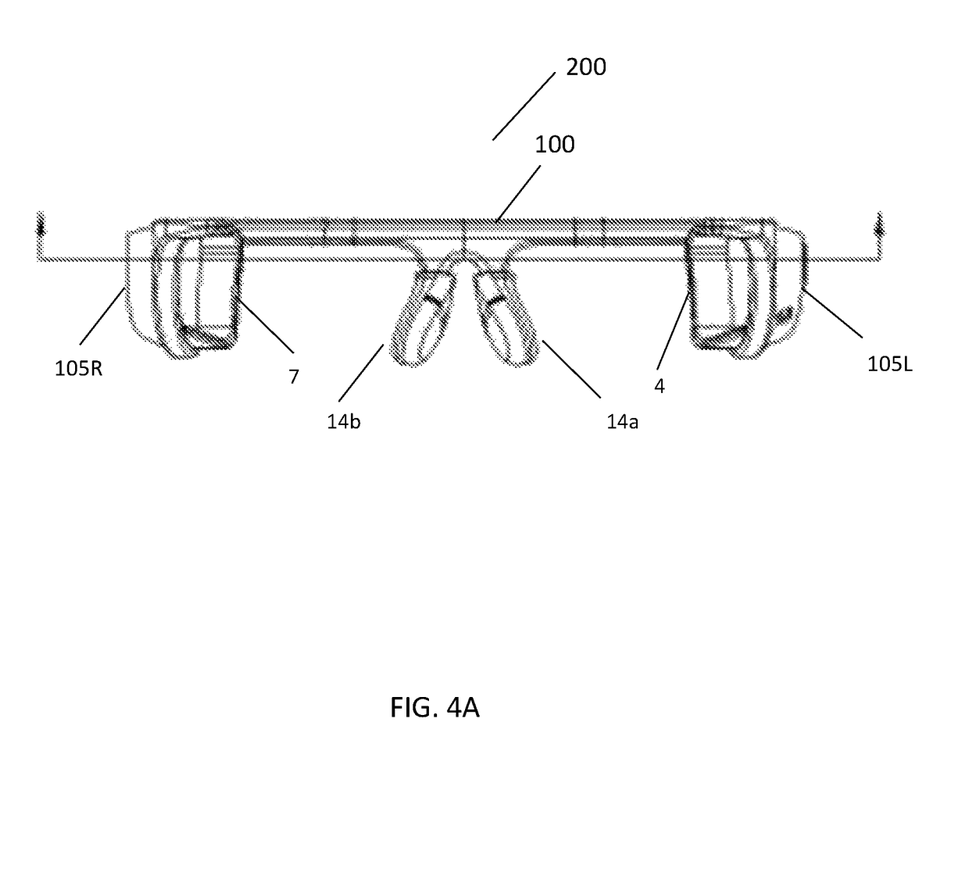
Figure 4B:
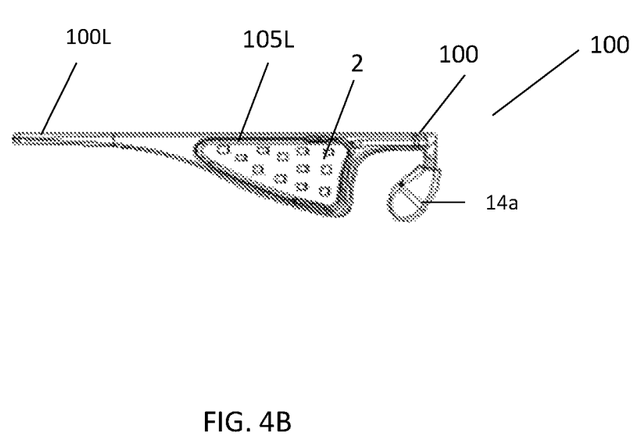

Referring to FIG. 4A, there is shown a cross sectional front view the eyewear phototherapy device 200 and side view of the eyewear phototherapy device 200 as shown in 4B. The LED light board 2 is clearly visible in the FIG. 4B.

Figure 5:
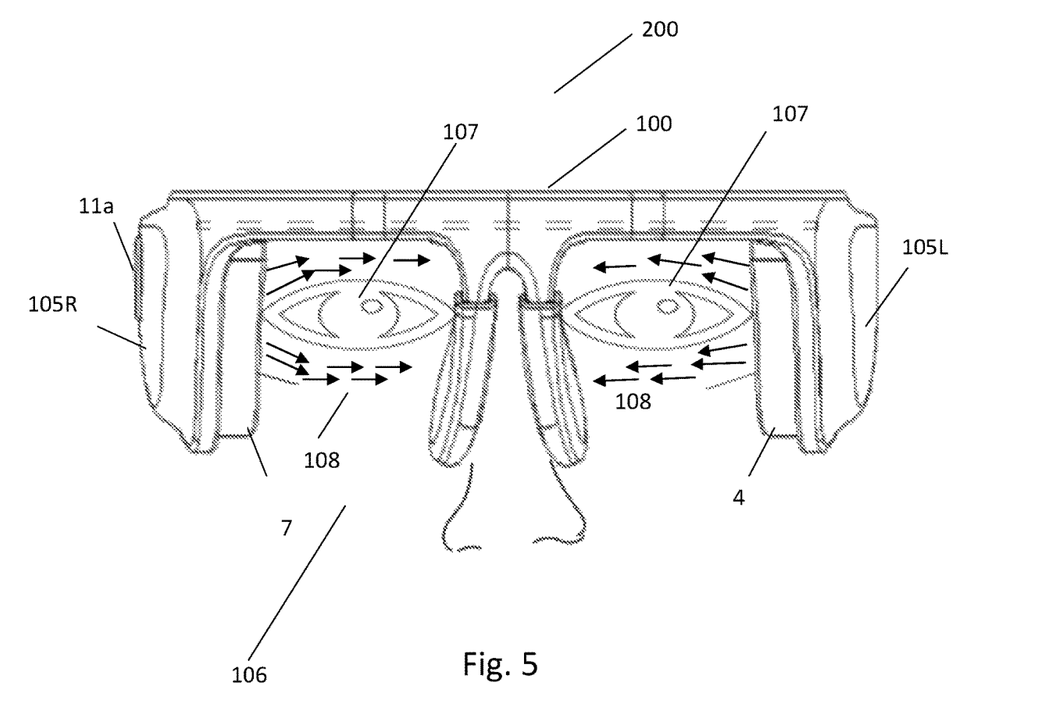
FIG. 5 delineates a pictorial representation of the eyewear when worn by a user, according to various embodiments of the present disclosure.

FIG. 5 represents an application of the above described eyewear phototherapy device 200 when worn by a user 106. As can be seen from the FIG. 5, the emissions 108 from the LED light boards (2, 2a) on the left and right sides of the device 200 are spread evenly on the skin surrounding the eyes 107 of the user 106. The arrows represent the movement of the LED emissions 108 over the skin. The protective elements (7, 4) ensures even spreading of the LED emission and thereby protecting the human eye from any damage.

The present eyewear phototherapy device would prove to be beneficial in providing anti-aging phototherapy wearable glasses treatment dedicated to anti-aging. This wearable eyewear device promotes collagen to generate a special mixture of photon energies to stimulate the fibroblasts around the eye, thereby enhancing collagen and elastin. Treatments through eyewear device deliver light energy into facial including eye parts tissue to help regenerate collagen and fibroblasts into the skin of the eyes as well as penetrate the skin and help eliminate wrinkles on the eyes. Continuing to use LED eyewear devices for a period of time, which takes about 15-30 days, will help to increase the elasticity and vitality of user eye's skin and help to relieve eye wrinkles.

The terms "a," "an," "the" and similar referents used in the context of describing the disclosure (especially in the context of the following claims) are to be construed to cover both the singular and the plural unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the disclosure and does not pose a limitation on the scope of the disclosure otherwise claimed. No language in the specification should be construed as indicating any non-claimed element essential to the practice of the disclosure.

It is contemplated that numerical values, as well as other values that are recited herein, are modified by the term "about", whether expressly stated or inherently derived by the discussion of the present disclosure. As used herein, the term "about" defines the numerical boundaries of the modified values so as to include, but not be limited to, tolerances and values up to, and including the numerical value so modified. That is, numerical values can include the actual value that is expressly stated, as well as other values that are, or can be, the decimal, fractional, or another multiple of the actual value indicated, and/or described in the disclosure.

Groupings of alternative elements or embodiments of the disclosure disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markus groups used in the appended claims.

Certain embodiments of this disclosure are described herein, including the best mode known to the inventors for carrying out the disclosure. Of course, variations on these described embodiments will become apparent to those of ordinary skill in the art upon reading the foregoing description. The inventor expects skilled artisans to employ such variations as appropriate, and the inventors intend for the disclosure to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

Although specific embodiments and certain structural arrangements have been illustrated and described herein, it will be clear to those skilled in the art that various other modifications and embodiments may be made incorporating the spirit and scope of the underlying inventive concepts and that the same is not limited to the particular methods and structure herein shown and described except insofar as determined by the scope of the appended claims.

What is claimed is:

1. An eyewear phototherapy device for providing skin cosmetology to skin surrounding the eyes, the eyewear phototherapy device comprising:
   a main spectacle frame having a left supporting member and a right supporting member, wherein both the left supporting member and the right supporting members include at least one respective housing assembly,
   wherein the at least one respective housing assembly extends outward from the each of the left and the right supporting members, and faces towards respective inner portions of the left and the right supporting members;
   wherein the at least one housing assembly comprises:
   an LED light board adapted to emit light energy in a direction transverse to the line of sight of a user, the LED light board being attached to the inner side of the at least one housing assembly, a transparent silicone cover attached to the LED light board for protecting against direct contact between the LED light board and human skin,
a controller circuit board connected to the LED light board, the controller circuit board being capable of controlling emissions from the LED light board,
at least one control button for receiving a user input, wherein the at least one control button is connected to the controller circuit board,
a battery unit for powering the LED light board, the controller circuit board and the at least one control button, and
at least one protective element which is adapted to prevent the LED emissions from entering a human eye, wherein the at least one protective element includes fixing elements for fixing the at least one protective element with the at least one housing assembly,
wherein the controller circuit board is adapted to receive the user input from the at least one control button and activate the LED light board to deliver emissions based on the user input.

2. The eyewear phototherapy device as claimed in claim 1, wherein the LED assembly is powered by the battery unit, the LED assembly delivering light energy into the facial area, including eye parts tissue, to help regenerate collagen and fibroblasts into the skin of the eyes and penetrate the skin to help eliminate wrinkles surrounding the eyes.

3. The eyewear phototherapy device as claimed in claim 1, wherein a housing assembly of the left supporting member includes a first battery unit, a first LED light board, a first transparent silicon cover and at least one first protective element;
wherein a housing assembly of the right supporting member includes a first control button, a first controller circuit board, a second LED light board, a second transparent silicon cover and at least one second protective element,
wherein the first control button, the first controller circuit board, the first battery unit, the first LED light board, and the second LED light board are interconnected via connecting wires; and
wherein the first controller circuit board is adapted to control the first battery unit, the first LED light board, and the second LED light board based on the user input received from the first control button.

4. The eyewear phototherapy device as claimed in claim 3, further comprising a hollow tube passing through the left supporting member, the right supporting member and the at least one housing assembly, wherein the hollow tube includes the connecting wires for connecting the components of the left supporting member and the right supporting member.

5. The eyewear phototherapy device as claimed in claim 3, wherein the first controller circuit board is adapted to separately control light intensity irradiated by the first LED light board and the second LED light board.

6. The eyewear phototherapy device as claimed in claim 3, wherein the at least one first control button is adapted to receive input from the user in regards to the right eye only.

7. The eyewear phototherapy device as claimed in claim 3, wherein the at least one housing assembly of the left supporting member includes at least one second control button which is adapted to received input from the user in regards to the left eye only.

8. The eyewear phototherapy device as claimed in claim 3, wherein the housing assembly of the left supporting member includes a second controller circuit board and the housing assembly of the right supporting member includes the first controller circuit board.

9. The eyewear phototherapy device as claimed in claim 3, wherein the at least one housing assembly of the left supporting member and the right supporting member includes the first battery unit and the second battery unit, respectively.

10. The eyewear phototherapy device as claimed in claim 1, wherein the controller circuit board includes a communication unit which is adapted to communicate with other computing devices via communication means.

11. The eyewear phototherapy device as claimed in claim 1, wherein the first control button and the second control button are located at the outer surface of the housing assembly.

12. The eyewear phototherapy device as claimed in claim 1, wherein the controller circuit board is configured to control a range of LED light emissions based on the user input.

13. The eyewear phototherapy device as claimed in claim 1, wherein the user can select the intensity of the LED emissions from at least one of low, medium and high.

14. The eyewear phototherapy device as claimed in claim 1 further comprising a display attached on the outer surface of the at least one housing assembly for displaying at least one information, wherein the display is connected to the controller circuit board and at least one control button.

15. The eyewear phototherapy device as claimed in claim 14, wherein the at least one information comprises a user selected mode such as low, medium and high, time duration of the therapy, type of alarm icon and combinations thereof.

16. The eyewear phototherapy device as claimed in claim 1, wherein the controller circuit board further comprises an audio device for providing audio alert notification based on a predefined parameter,
wherein the predefined parameter is any one of a warning of low battery, an expiration of therapy time, a communication establishment notification, a failure of apparatus component, a battery replacement and combinations thereof.

17. The eyewear phototherapy device as claimed in claim 1, wherein the at least one control button allows a user to set time duration for the therapy.

18. The eyewear phototherapy device as claimed in claim 1, wherein the left supporting member and the right supporting member, respectively, includes a curved left nose arm and a curved right nose arm extending downwards from a joining point on the main spectacle frame, wherein the curved left nose arm and the curved right nose arm upon connecting with the main spectacle frame, create a nose support below the joining point,
wherein the left supporting member, the curved left nose arm, and a left lens support create a left receptacle; and
wherein the right supporting member, the curved right nose arm, and a right lens support create a right receptacle such that the left receptacle and the right receptacle accommodate a user desired glass or lens; and
wherein the left lens support and the right lens support are flexible and adjustable which helps in accommodating the user desired glass or lens within the left receptacle and the right receptacle respectively.

19. The eyewear phototherapy device as claimed in claim 1, wherein multiple LED elements of the LED light board are assigned to specific areas of the skin surrounding the eyes.

* * * * *